US012648763B2

(12) United States Patent
Freeman et al.

(10) Patent No.: US 12,648,763 B2
(45) Date of Patent: Jun. 9, 2026

(54) REFLEX HAMMER WITH SENSORS

(71) Applicant: Vade Mecum LLC, Jacksonville, FL (US)

(72) Inventors: William David Freeman, Jacksonville, FL (US); Mark Philip Grek, Jacksonville Beach, FL (US)

(73) Assignee: Vade Mecum LLC, Jacksonville, FL (US)

( * ) Notice: Subject to any disclaimer, the term of this patent is extended or adjusted under 35 U.S.C. 154(b) by 654 days.

(21) Appl. No.: 17/247,735

(22) Filed: Dec. 21, 2020

(65) Prior Publication Data

US 2022/0192641 A1      Jun. 23, 2022

(51) Int. Cl.
    *A61B 9/00*          (2006.01)
    *A61B 5/00*          (2006.01)
    *A61B 5/06*          (2006.01)

(52) U.S. Cl.
    CPC .............. *A61B 9/005* (2013.01); *A61B 5/067* (2013.01); *A61B 5/4523* (2013.01)

(58) Field of Classification Search
    CPC ....... A61B 9/005; A61B 5/067; A61B 5/4523; A61B 5/0053
    See application file for complete search history.

(56) References Cited

U.S. PATENT DOCUMENTS

2007/0167888 A1* 7/2007 Taylor .................. A61H 1/0292
                                                           601/84
2010/0106059 A1* 4/2010 Zhang ................... A61B 9/005
                                                           600/587

2014/0206953 A1* 7/2014 Valdastri .............. A61B 5/0031
                                                           600/301
2021/0275152 A1* 9/2021 Slepian .................. A61B 5/395
2021/0361336 A1* 11/2021 Adekanmbi .......... A61F 2/4657
                        (Continued)

FOREIGN PATENT DOCUMENTS

CA        2980454 A1    3/2019
CN     106725625 A  *  5/2017  ........... A61B 5/0053
                        (Continued)

OTHER PUBLICATIONS

"International Application Serial No. PCT/US2021/072990, International Search Report mailed Feb. 24, 2022", 5 pgs.
                        (Continued)

*Primary Examiner* — Jason M Sims
*Assistant Examiner* — Ari S Padda
(74) *Attorney, Agent, or Firm* — Schwegman Lundberg & Woessner, P.A.

(57)          ABSTRACT

A system includes a first device having a handle, a head coupled to the handle, a bumper supported by a first end of the head and adapted to be used to strike a patient tendon, a force sensor coupled to the bumper and adapted to generate force data in response to force encountered by the bumper and to generate force data, a first accelerometer coupled to generate head acceleration data in response to movement of the head, and first circuitry to capture the force data and acceleration data. The system may further include second device having a housing adapted to be coupled to the patient limb, a second accelerometer supported by the housing to generate limb acceleration data, and second circuitry to capture the acceleration data.

18 Claims, 7 Drawing Sheets

(56)        References Cited

U.S. PATENT DOCUMENTS

2023/0181169 A1 *   6/2023   Wright .................... A61B 9/00
                                                              600/553
2025/0176949 A1     6/2025   Freeman et al.

FOREIGN PATENT DOCUMENTS

CN        107157518 A  *  9/2017   ........... A61B 5/0053
JP        2006034809 A     2/2006
WO        2019141537       7/2019
WO    WO-2019241412 A1    12/2019
WO    WO-2022140746 A1     6/2022

OTHER PUBLICATIONS

"International Application Serial No. PCT/US2021/072990, Written Opinion mailed Feb. 24, 2022", 7 pgs.
Meinhold, Waiman, et al., "An Instrumented Medical Hammer With Diagnostic, Therapeutic and Pedagogical Applications", Proceedings of the ASME 2017 Dynamic Systems and Control Conference, (2017), 6 pgs.
"European Application Serial No. 21844592.2, Communication Pursuant to Article 94(3) EPC mailed Jun. 25, 2025", 5 pgs.

* cited by examiner

REFLEX HAMMER WITH SENSORS

BACKGROUND

The gold-standard for clinical localization-related diagnosis of neurological health and disease states for both central nervous system (CNS) and peripheral nervous system (PNS) disorders is centered around assessment of deep tendon reflexes (DTR) using a reflex hammer (RH) tool. The RH tool and DTR-based method of physical exam originated in the late 1800's and predate any neuroimaging such as CT and MRI classification of neurological disease. The basis of the DTR method of neurologic exam is based on structural integrity of the CNS-PNS corticospinal tract that originates in the cortex, descends through the brain to the spinal cord and exists into the peripheral nerve and finally synapses within muscles spindles and the heavy myelinated neurons of the Golgi tendon organs (GTO).

Assessment of DTR reflexes using an RH tool however is largely qualitative by human visual estimation of the degree of limb movement in response to tapping a DTR site. In 1943, the Medical Research Council (MRC) created a Likert scale for muscle strength grading which was adapted to DTR's NINDS scale in 1993. The MRC muscle and NINDS reflex scales are taught in medical schools and over time refined by neurology postdoctoral physician training on hundreds of patients. The MRC ranges from 0-4 with 2 considered normal, 0-1 being absent to barely present, and 3 to 4 being pathologically hyperactive responses. Unfortunately, there has been little to no advancement since the late 1800's on this exam technique or since the semi-quantitative visual method proposed by the MRC. Mayo Clinic later devised their own DTR scale with (Table 1) with 9 levels of DTR classification. Both the Mayo and NINDS scales (Table 2) were later compared in a prospective inter-rater reliability study and unfortunately both showed poor correlation.

TABLE 1

Mayo Clinic scale for tendon reflex assessment[3]

| Description | Score |
| --- | --- |
| Absent | −4 |
| Just elicitable | −3 |
| Low | −2 |
| Moderately low | −1 |
| Normal | 0 |
| Brisk | +1 |
| Very brisk | +2 |
| Exhaustible clonus | +3 |
| Continuous clonus | +4 |

TABLE 2

NINDS scale for tendon reflex assessment[1]

| Description | Score |
| --- | --- |
| Reflex absent | 0 |
| Reflex slight, less than normal: includes a trace response or a response brought out only by reinforcement | +1 |
| Reflex in lower half of normal range | +2 |
| Reflex in upper half of normal range | +3 |
| Reflex enhanced, more than normal: includes a clonus if present which optionally can be noted in an added verbal description of the reflex | +4 |

Therefore, there remains diagnostic imprecision and inaccuracy in neurological diagnosis due to heterogeneity in exam precision and accuracy. Diagnostic exam accuracy and precision are absolutely critical to timely diagnosis such as the neurological emergency of Guillain Barre syndrome (GBS). GBS is an autoimmune disorder of the peripheral nervous system often triggered by upper respiratory or gastrointestinal (GI) illnesses, sometimes other autoimmune antibody states, and even cancer-triggered states called paraneoplastic disorders. Because of the lack of accurate examination findings, GBS diagnoses is often delayed by days to weeks and patients often end up intubated and mechanically ventilated and transferred to an academic teaching hospital for a neurologist skilled DTR and diagnostic assessment.

One of the hallmarks on physical examination is the acute loss of DTR's in the proper clinical setting with a history of acute/subacute onset paresthesia and muscle weakness with or without an antecedent viral or GI illness. Another neuromuscular disorder often mis-diagnosed due to lack of neurological examination by weeks to months later is Myasthenia gravis, which is another autoimmune disorder that attacks the neuromuscular junction with antibodies binding to the nicotinic acetylcholine receptor on skeletal muscle. MG typically has preservation of DTR's in contrast to GBS with another hallmark being fatigueable weakness improving with rest. Further at least 20 million people in the United States have peripheral neuropathy which can lead to reduced DTR's in the late stages.

SUMMARY

A system includes a first device having a handle, a head coupled to the handle, a bumper supported by a first end of the head and adapted to be used to strike a patient tendon, a force sensor coupled to the bumper and adapted to generate force data in response to force encountered by the bumper and to generate force data, a first accelerometer coupled to generate head acceleration data in response to movement of the head, and first circuitry to capture the force data and acceleration data.

The system may further include second device having a housing adapted to be coupled to the patient limb, a second accelerometer supported by the housing to generate limb acceleration data, and second circuitry to capture the acceleration data.

DETAILED DESCRIPTION

Figure 1:
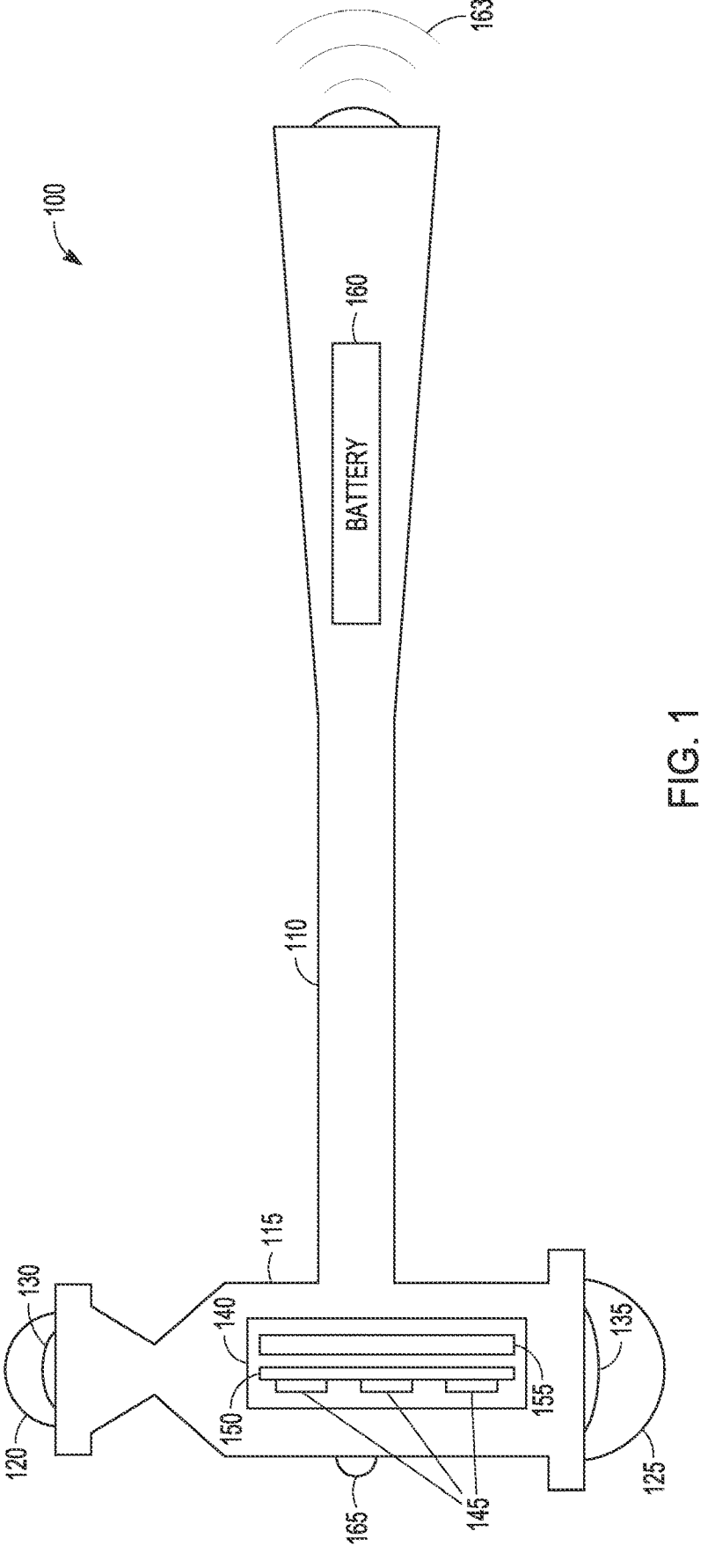
FIG. 1 is a block diagram of a smart reflex hammer according to an example embodiment.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software in one embodiment. The software may consist of computer executable instructions stored on computer readable media or computer readable storage device such as one or more non-transitory memories or other type of hardware based storage devices, either local or networked. Further, such functions correspond to modules, which may be software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system, turning such computer system into a specifically programmed machine.

The functionality can be configured to perform an operation using, for instance, software, hardware, firmware, or the like. For example, the phrase "configured to" can refer to a logic circuit structure of a hardware element that is to implement the associated functionality. The phrase "configured to" can also refer to a logic circuit structure of a hardware element that is to implement the coding design of associated functionality of firmware or software. The term "module" refers to a structural element that can be implemented using any suitable hardware (e.g., a processor, among others), software (e.g., an application, among others), firmware, or any combination of hardware, software, and firmware. The term, "logic" encompasses any functionality for performing a task. For instance, each operation illustrated in the flowcharts corresponds to logic for performing that operation. An operation can be performed using, software, hardware, firmware, or the like. The terms, "component," "system," and the like may refer to computer-related entities, hardware, and software in execution, firmware, or combination thereof. A component may be a process running on a processor, an object, an executable, a program, a function, a subroutine, a computer, or a combination of software and hardware. The term, "processor," may refer to a hardware component, such as a processing unit of a computer system.

Furthermore, the claimed subject matter may be implemented as a method, apparatus, or article of manufacture using standard programming and engineering techniques to produce software, firmware, hardware, or any combination thereof to control a computing device to implement the disclosed subject matter. The term, "article of manufacture,"

as used herein is intended to encompass a computer program accessible from any computer-readable storage device or media. Computer-readable storage media can include, but are not limited to, magnetic storage devices, e.g., hard disk, floppy disk, magnetic strips, optical disk, compact disk (CD), digital versatile disk (DVD), smart cards, flash memory devices, cloud based storage, smart phone memory and others. In contrast, computer-readable media, i.e., not storage media, may additionally include communication media such as transmission media for wireless signals and the like.

A smart reflex hammer includes sensors to provide Quantitative Newtonian RefleXometry (Q-NRX) for accurate medical diagnosis in neurological health and other medical diseases. The smart reflex hammer may include a wireless transceiver to transmit sensor data responsive to use of the hammer on subjects.

A valid reflex visually is seen by the swing of the leg for example during knee reflex test. Tapping a reflex hammer on the patellar tendon generates neural feedback from the nerves to the spinal cord and back to the muscle to counteract the tendon stretch preventing injury to the muscle and tendon. The smart reflex hammer provides data from the sensors that quantifies several components of the neurological deep tendon reflexes including acceleration and velocity of the hammer, and amplitude of the reflex similar to pendulum action and back.

Disease states may be determined by classifying reflexes and the associated nervous system into three general classes, normal reflex, hyperactive reflex and hypoactive or absent reflexes. Such classification has been performed visually by health care professionals personally observing patient responses to hammer strikes. Normal reflex velocity and amplitude is quantified by the semi-quantitative Medical Research Council (MRC) scale. Hyperactive reflexes indicate potential upper motor neuron lesions within the central nervous system (CNS) and are hyper reflexive in terms of amplitude and velocity. Hypoactive or absent reflexes indicate lower motor neuron diseases or peripheral nerve diseases or acute spinal shock.

The MRC has at least two challenges for scaling the neurological exam globally. There are considerable inter-rater reliability differences from novice to expert and among different health care professionals. In addition, MRC is semi-quantitative and best done by neurologists who spend years in training to recognize the subtleties and range of normal and abnormal findings. The smart reflex hammer helps by providing highly quantitative reflex measurements in terms of amplitude and velocity. By obtaining quantitative information utilizing the smart reflex hammer, a baseline may be created, and trends or changes can be later assessed. For example, Guillain Barre syndrome is characterized as progressive sensory motor dysfunction, loss of power to ambulate, and nearly always areflexia or loss of any reflex response. Changes and progressive loss of reflexes over time or documentation of reflex recovery therefore are critical to future therapeutic interventions in Guillain Barre and many other neurological diseases.

FIG. 1 is a block diagram of a smart reflex hammer 100 according to an example embodiment. Hammer 100 may have an exterior shape that is similar to existing reflect hammers, with a handle 110 coupled to a head 115. The head has a first bumper 120 on a first end, and optionally a second bumper 125 on a second end. The bumpers may be different sizes in some embodiments, or only one bumper may be used in further embodiments.

Each bumper 120, 125 has a corresponding respective embedded impact force sensors 130, 135. Force Sensors detect and respond to the presence or a change in the amount of pressure on an actuator, which can be a ball, button, diaphragm, flat membrane, plunger, or pushbutton. Three example sensor types are force sensing resistor, load cell, and resistive. The bumper material may be constructed of plastic in some embodiments and is configured to ensure that force from a bumper contacting a tendon of a patient is transferred to the corresponding force sensor. In various embodiments, the bumpers may be supported by the force sensors, or may be sufficiently compliant to consistently transfer force from impacts to the pressure sensor, yet firm enough to trigger sufficient reflex response. In some embodiments, data is generated by the force sensors 130, 135 representative of pounds per square inch (PSI) or pascals on the sensor. Calibration for each hammer may be performed on manufacture to account for manufacturing tolerances by testing each hammer using consistent striking force and surface impacts.

Head 115 may also include an electronics cavity 140 that substantially rigidly supports one or more inertial measurement units (IMUs) such as gyros or accelerometers 145 that provide 6 degree of freedom sensor measurements corresponding to acceleration of the hammer. Velocity of the hammer can be derived from the sensor acceleration measurements. The electronics cavity 140 may also include circuitry 150, and a power source, such as a battery 155. The circuitry 150 may collect and process data corresponding to measurements of acceleration and pressure from the multiple sensors that can be used to classify reflex reactions. Data generated based on sensed force and acceleration may be referred to as telemetry data. Circuitry 150 may also provide for calibration of sensor data, such as pressure. In addition, circuitry 150 may be located in the electronics cavity 140 or elsewhere in the hammer 100, such as handle 110.

Hammer 100 may also include an additional or alternative battery 160 which may be located in the handle 110. An antenna 163 may be coupled to the circuitry 150 and used to transmit and receive data from other devices. The Antenna 163 is shown coupled to an end of the handle 110 opposite the head 115 but may be located anywhere suitable for transmitting and receiving data by the circuitry 150. A display 165 may be positioned on the head 115 and coupled to circuitry 115. Display 165 may include one or more light emitting diodes or other means of displaying information in some embodiments and may be used to display the status of various components, such as batteries and accelerometer sensors.

The use of multiple accelerometers 145 or IMU devices can provide redundancy and diversity for medical applications, the smart hammer 100 may deploy multiple devices, either by the same or by different manufacturers, in the same or different orientations. Specifically, this addresses intrinsic silicon or micro-electromechanical systems (MEMS) noise issues with high gain systems, such as discerning very low amplitude movements or trying to isolate small differences in absolute value.

The impact/force sensors 130, 135 may be layered; that is more than one force sensor with different force ranges to measure a single impact. This approach of applying multiple sensors with different materials will have the benefit of incorporating overlaying dynamic ranges. The hammer 100 may also make use of a custom force sensor that includes a hole in the sensor, or a force sensor suspended in room-temperature-vulcanizing (RTV) silicone or rubberized head/bumper.

The antenna 163 may be integrated into the handle with the radiating element positioned furthest away from the hammer head, using the handle and head an integral component to radio frequency (RF) reception. This physical structure will optimize RF network connectivity for transfer of telemetry data.

The hammer display 165 may be used to indicate the operational status or states of the smart hammer 100. The states may include but are not limited to battery status—good, bad, charging, charged, IMU/Accelerometer status—fault, OK, Force/Impact status—fault, OK.

The display 165 can uniquely perform the function of visually displaying impact strength, vector quality (the angle of impact on the tendon) in either absolute or relative terms. This includes but is not limited to changing color. The display can multimode in terms of displaying velocity/response strength from the telemetry device.

Sensors and electronics of the smart hammer can either be integrated into an add-on module for use non-OEM or generic hammers. In one example, all the electronics and sensors may be integrated into a replaceable head 115 for use with various handles. In a further example, the electronics and sensor may be integrated into a replaceable bumper. In still further embodiments, bumpers with sensors may be provided with suitable connectors to mate with connectors in the head 115 such that various sized bumpers may be used with the hammer 100.

Figure 2:
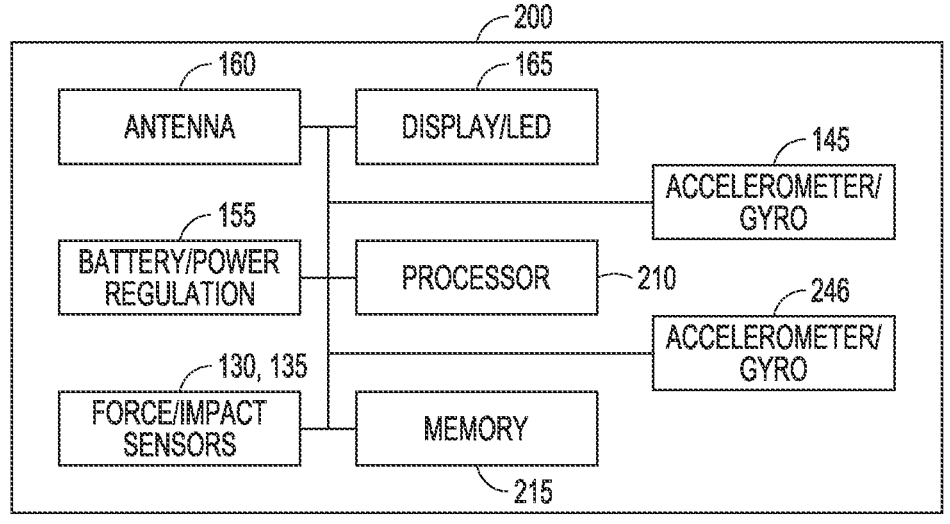
FIG. 2 is a block diagram illustrating a system comprising circuitry for collecting and processing data related to smart hammer strikes.

FIG. 2 is a block diagram illustrating a system 200 comprising circuitry for collecting and processing the telemetry data related to smart hammer strikes. In one embodiment, system 200 includes elements that may be disposed within electronics cavity 140 of smart hammer 100. Like elements in FIG. 2 are labeled with like reference numbers from FIG. 1.

System 200 includes a processor 210 and associated memory 215 on which programming is stored for execution by processor 210 to implement one or more methods. The processor 210 and memory 215 comprise circuitry 140 and may be mounted on a circuit board or other suitable substrate.

A communication bus 220 may be used to couple the processor 210 and memory 215 to the battery 155, sensors 130, 135, accelerometer 145, and display 165. An addition accelerometer 246 may be coupled to the communication bus 220 and may be oriented differently from accelerometer 145. The orientation may be orthogonal in one embodiment to ensure diversity of data in sensing acceleration.

Figure 3:
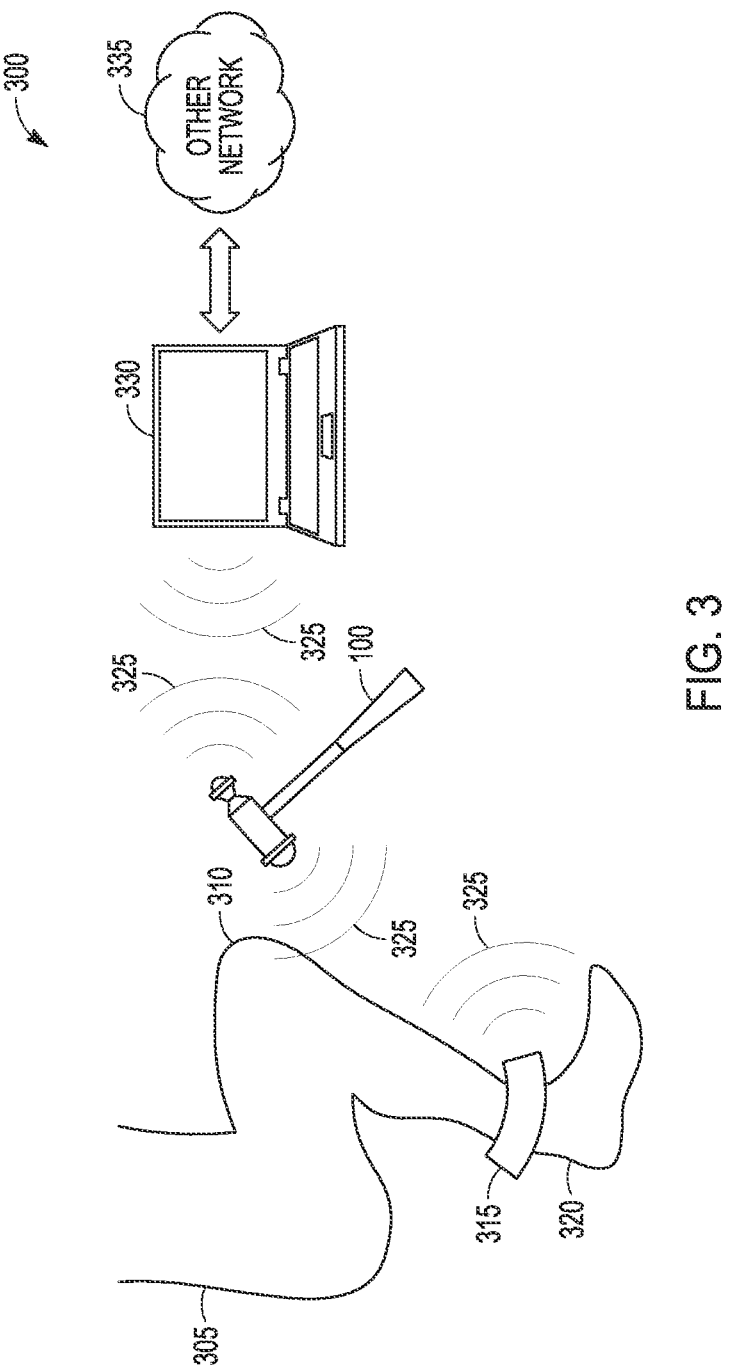
FIG. 3 is a block representation of a system for measuring reflex reactions according to an example embodiment.

FIG. 3 is a block representation of a system 300 for measuring reflex reactions. System 300 includes a smart hammer, such as smart hammer 100 for use in contacting a patient 305 tendon, such as at a knee 310 of the leg. A patient telemetry monitor/device 315 is shown as being worn by the patient 305, such strapped to an ankle 320 of the leg. Device 315 may include one or more accelerometers for sensing and generating telemetry data representative of movement of the leg of the patient 305 in response to the smart hammer 100 striking the knee 310.

The monitor device 315 and smart hammer 100 may form a wireless Medical Area Network (MaN) indicated generally at 325. A monitoring station 330 and associated network 335 or other portable monitoring device such as a smartphone and its corresponding network. The monitoring station 330 may collect data from the smart hammer 100 and device 315. The collection of the inertial movement and force impact information is generally coordinated by a processor, where that information and or computed or manipulated derivatives thereof are made available to the wireless MaN interface 325, visual display indication 165 of the smart hammer 100, or both. The processor may be one or more of the processors in the smart hammer 100, device 315, and monitoring station 330, operating together or independently. Functions may be distributed in any desired manner in some embodiments.

While data, including the telemetry data, from the devices in the network 325 can flow between the hammer 100, monitor device 315 and the monitoring station 330 or multiple stations such as a computer, tablet, smartphone or similar device, the telemetry data can be logged locally for later download, or aggregated and compiled for real time direction for machine learning or other database-derivative type analysis and comparison. The database or machine learning can be a local computer application, or the telemetry data can be forwarded to a server, network, or cloud-based computing platform where MaN data will be processed via network 335 by cloud based resources.

Automatic data collection from hammer 100 may be performed by station 330 when connected, or when the hammer 100 becomes connected, either wirelessly or via USB or other physical connection. In one embodiment, the connection and collection may be initiated with sensed proximity to station 330, which may be a data collection or charging/wireless charging unit equipped with a data telemetry interface. One practical use case is that proximity to an station 330 comprising a mobile device such as an iPhone® may automatically cause the hammer 100 or ankle device 315 to wake up and download to the station 330. Station 330 may also be a wireless bridge to interface to a hospital network and even provide for automatic updating of electronic medical records with suitable security for HIPA compliance. In one embodiment, each wireless connection herein may be provided with encryption for data security. An encrypted key either fixed, public, private, or randomly generated may be used for the purposes of device authentication, pairing, and data validity checks.

Once the telemetry data is processed, the information along with comparison and contrast information unique to the immediate or stored patient response can be presented on the smartphone, tablet, PC, or similar monitor device 330. In some cases, the monitor device can communicate directly with the hammer 100 and device 315 circuitry and logic via network 325 or network 335 in the case of each device having its own IP address. The monitor device 330 may alternatively contain some shared component of the AI/ML processing algorithm, or may wholly contain the AI/ML comparison/contrast algorithm or model for the purposes of patient assessment and to store real-time telemetry data.

Figure 4:
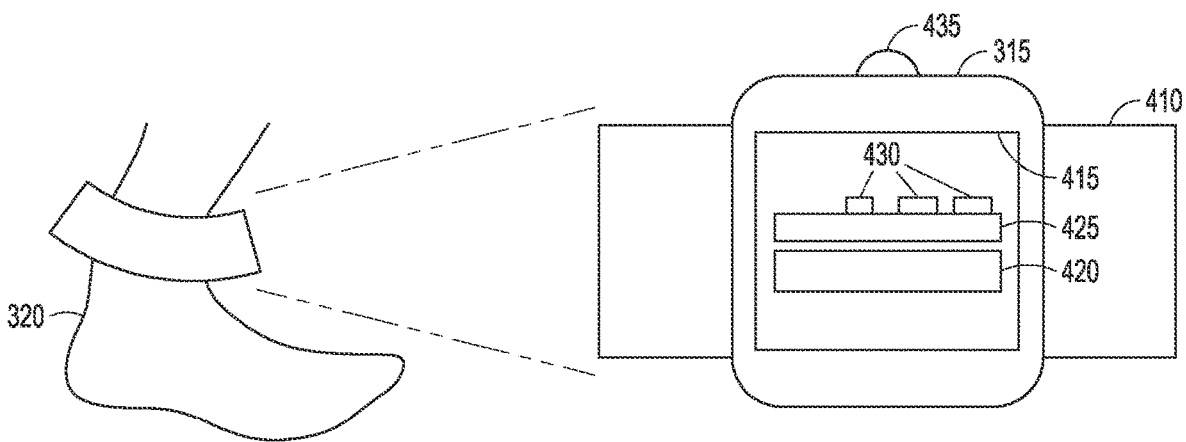
FIG. 4 is a block diagram view of a monitor device according to an example embodiment.

FIG. 4 is a block diagram view of monitor device 315. Device 315 in one embodiment is coupled to a strap or band 410, such as an elastic strap configured to retentively retain the device 315 to the ankle of the patient during movement of the leg of the patient. The band 410 may also be adapted/adjusted to apply the device 315 to other patient limbs, extremities, or digits in further embodiments. Similarly to smart hammer 100, the device 315 includes an electronics cavity 415 that supports a batter 420, electronics 425, and one or more accelerometers 430. A display 435, such as one or more LEDs may also be supported by the device 315 in a position such that it is visible to a health professional performing reflex diagnostics. Note that both devices, including the hammer 100 and monitor device 315 may include power buttons to turn on the devices for use. In further embodiments, motion sensors may be used in a sleep mode to fully power on the devices for use. Display 165 may display light of different frequencies or certain repeating series of blinks to indicate that one or both the devices are ready for use. Monitor device 315 may also have a separate display.

Figure 5:
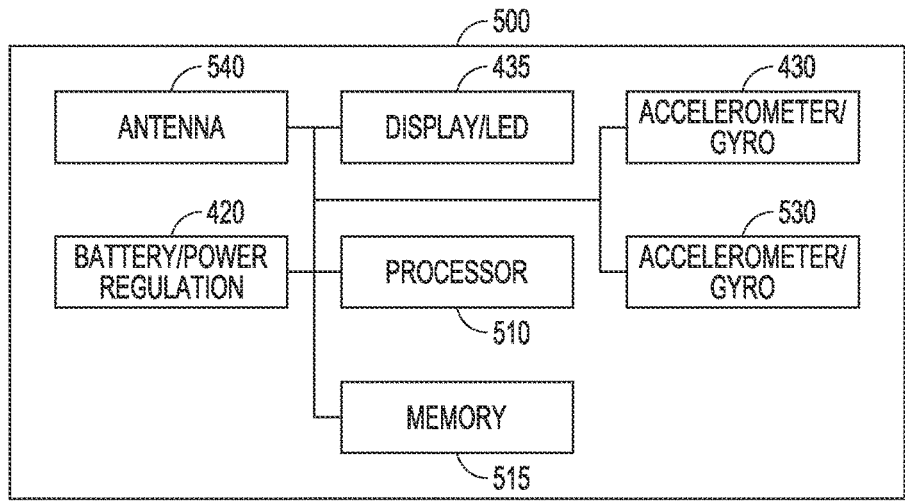
FIG. 5 is a block diagram illustrating a system comprising circuitry for collecting and processing data related to smart hammer strikes according to an example embodiment.

FIG. 5 is a block diagram illustrating a system 500 comprising circuitry for collecting and processing data related to smart hammer strikes. In one embodiment, system 500 includes element that may be disposed within a sealed electronics cavity 415 of device 315. Like elements in FIG. 5 are labeled with like reference numbers from FIG. 4.

System 500 includes a processor 510 and associated memory 515 on which programming is stored for execution by processor 510 to implement one or more methods. The processor 510 and memory 515 comprise circuitry 425 and may be mounted on a circuit board or other suitable substrate.

A communication bus 520 may be used to couple the processor 510 and memory 515 to the battery 420, accelerometer 430, and display 435. An addition accelerometer 530 may be coupled to the communication bus 520 and may be oriented differently from accelerometer 430. The orientation may be orthogonal in one embodiment to ensure diversity of data in sensing acceleration. An antenna 540 may be coupled to the bus 520 for transmitting information via the MaN network. Blocks representing antennas may also be representative of transceivers operating in conjunction with the antennas and processors herein to send and receive data.

Figure 6:
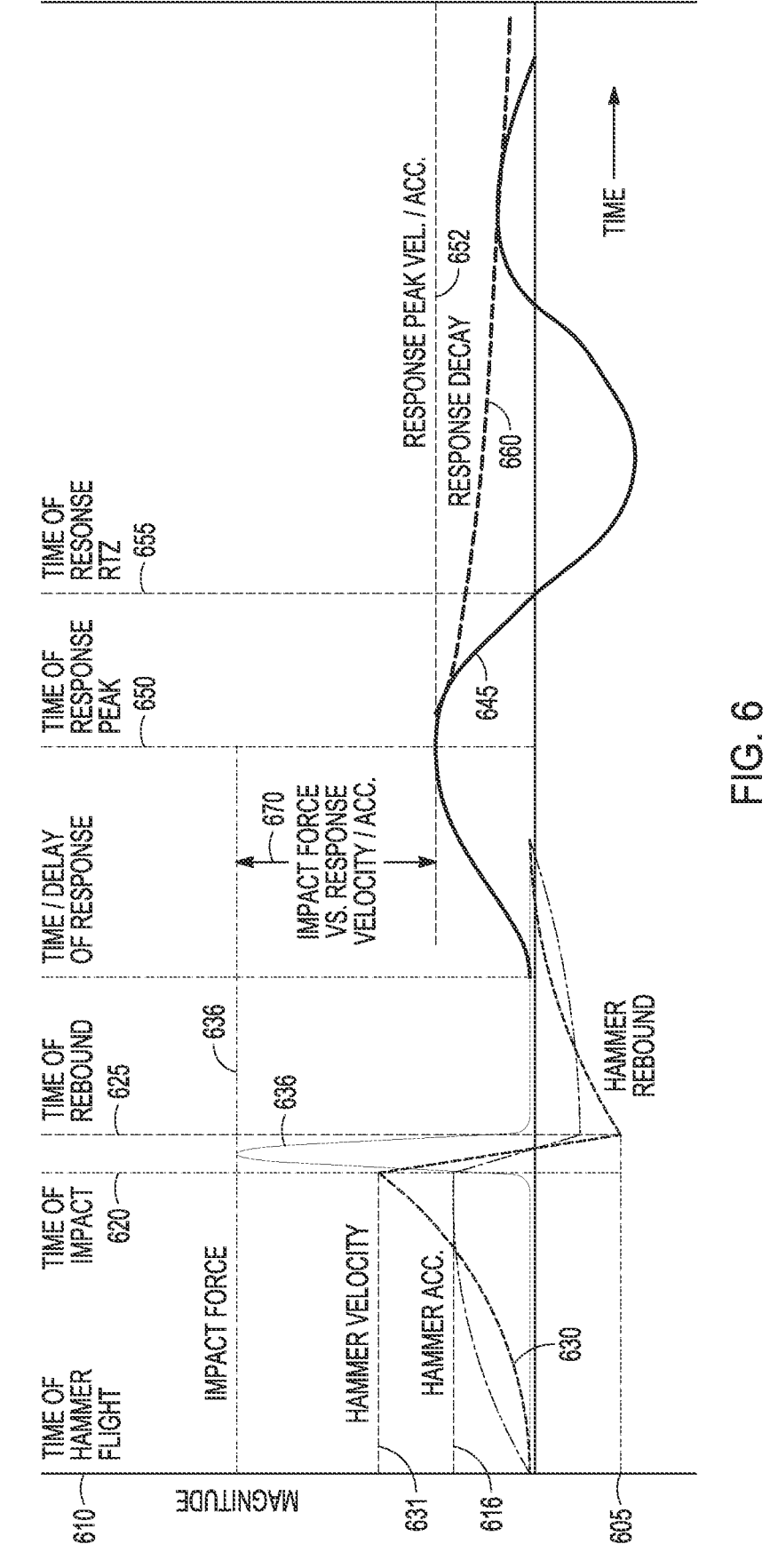
FIG. 6 is a graph illustrating data collected (telemetry) as a function of magnitude versus time according to an example embodiment.

FIG. 6 is a graph illustrating data collected (telemetry) from an example use of the smart hammer 100 and patient telemetry monitor/device 315 on a patient as a function of magnitude versus time. Time starts as indicated at time zero at 605. The magnitude axis 610 is relative for each type of data collected or derived. Metrics derived from the telemetry may include one or more of various magnitudes, shapes of inflection, types of inflections, time differences between one or more inflections and/or peaks, or series of combinations thereof.

In one embodiment, a synchronization pulse is shared between the hammer 100 and monitor device 315. The synchronization pulse may be provided through the monitor station 330 via the network 325 to the hammer 100 and monitor device 315 to coordinate absolute time or otherwise time sync or pulse. In further embodiments, any of the components coupled to network 325 may generate the synchronization pulse. The purpose of this synchronization is to coordinate and normalize the independent telemetry gathered by the hammer 100 and one or more monitor devices 315. In this way, patient response characteristics such as time from the impact of the hammer and initial patient response can be precisely quantified.

Between synchronization sequences, the hammer 100, monitor device or devices 315, and other system components will keep track of time internally with precision references. When data is downloaded for analysis, time stamps or counter values can be used from each device to determine differences in time. As an example, the individual times from the hammer 100 and monitor device 315 can be separately downloaded, where the absolute time difference between the two events can be determined by virtue of the synchronization activity.

In one embodiment, data is collected and time stamped. Counter stamps may alternatively be used. The time or counter stamps may have the same reference time or count as established by the synchronization pulse, which may be broadcast periodically, with the period selected based on the known accuracy of clocks or counters in each device. Graph 600 shows a starting at time zero 605 as hammer movement begins. Time zero 605 may be determined based on detection of increasing acceleration of the hammer 100. Hammer 100 acceleration is represented by an acceleration curve 615.

In one embodiment, absolute time and date information can be appended to strike and accelerometer data (telemetry) by a synchronizing device during the moment of download, synchronization, or post processing through the use of unique record IDs for each data point. In one embodiment, the unique record IDs differentiate each record, may be sequential in nature, and thereby define the relative time between each data point.

In one embodiment, acceleration of the hammer is near zero at time zero and is shown as gradually increasing to a peak hammer acceleration at 616 in a non-linear manner until a time of impact indicated at 620, at which point it quickly decreases until a time of rebound 625. Note that the time of impact 620 may be determined based on one or both of the acceleration data or the force data. For instance, a sudden deceleration can be indicative of impact, with the beginning of the deceleration being correlated to the time of impact. The start of a sudden increase in force is also indicative of impact.

A velocity curve 630 is shown as increasing from time zero 605 to a maximum velocity 631 until time of impact 620, and thereafter quickly decreasing until time of rebound 625. Thereafter, the velocity gradually increases. Note that the velocity can be determined from the acceleration curve 615 by integrating the acceleration times time.

Impact force begins at time of impact 620 and is illustrated by impact force curve 635. The impact force increases from zero quickly, reaches a peak impact force 636 and then decreases back to zero about the time of rebound 625.

Data from device 315 begins in response to the hammer strike at a time delay of response 640. A curve 645 represents acceleration, and hence velocity, of the leg in one example. A peak response time 650 corresponds to the maximum acceleration 652, which then decreases up to a time of response return to zero 655. Note that the leg continues to move back and forth as represented by the oscillation of the acceleration curve 645 about the zero of the magnitude axis. A response decay curve is shown at 660, tracking maximums of the oscillations.

The data collected may be used at a minimum, to determine a difference in time between impact and delay of response, which can be correlated to one or more patient conditions, including normal responses. Data related to the smart hammer may be utilized to determine whether the strike was a valid strike or not. For instance, a low impact force may not be sufficient to obtain a response that is adequate for the determined different in time between impact and response to be valid. Other data, such as the response peak and impact force to response velocity difference, indicated at 670 may be correlated to other patient conditions. The response decay curve 652 and oscillations of the response curve 645 may be correlated to further patient conditions. These correlations may be made via conducting tests and correlating resulting data to known patient conditions.

In further embodiments, the collected data max be correlated to one or more of the existing tables described above via health care professionals' visual observations using the smart hammer and comparing to the collected data. In one example, the collected data may be correlated to the NINDS scale for tendon reflex assessment. In a simplified correlation, a health professional may use the smart hammer to obtain telemetry data for an example number of patients, such as 100 patients. At the same time, the health professional may visually assess the response and label each example. Just using the response peak data, ranges of response peaks may then be established that correlate to the NINDS scale and saved in a reference table. New telemetry can then simply be compared to the table to select the proper scale label. For example, a response peak of zero corresponds to a score of zero on the Ninds scale. A response peak ranges may also be correlated to reflex slight score of +1, reflex in lower half of normal range score of +2, etc.

Correlations to other scales and conditions may similarly be made based on the response peak, as well as response peak in relation to impact force, time delay of response, decay of response, and other telemetry data obtained from either data from the smart hammer alone, the patient device alone, or a combination of data from each.

In still further embodiments, a machine learning model may be trained based one or more of the telemetry data that is labeled with a class identified by the health professional. One or more classes may correspond to a response table or even to a patient diagnosis or condition as desired.

Artificial intelligence (AI) is a field concerned with developing decision making systems to perform cognitive tasks that have traditionally required a living actor, such as a person. Artificial neural networks (ANNs) are computational structures that are loosely modeled on biological neurons. Generally, ANNs encode information (e.g., data or decision making) via weighted connections (e.g., synapses) between nodes (e.g., neurons). Modern ANNs are foundational to many AI applications, such as automated perception (e.g., computer vision, speech recognition, contextual awareness, etc.), automated cognition (e.g., decision-making, logistics, routing, supply chain optimization, etc.), automated control (e.g., autonomous cars, drones, robots, etc.), among others.

Many ANNs are represented as matrices of weights that correspond to the modeled connections. ANNs operate by accepting data into a set of input neurons that often have many outgoing connections to other neurons. At each traversal between neurons, the corresponding weight modifies the input and is tested against a threshold at the destination neuron. If the weighted value exceeds the threshold, the value is again weighted, or transformed through a nonlinear function, and transmitted to another neuron further down the ANN graph—if the threshold is not exceeded then, generally, the value is not transmitted to a down-graph neuron and the synaptic connection remains inactive. The process of weighting and testing continues until an output neuron is reached; the pattern and values of the output neurons constituting the result of the ANN processing.

The correct operation of most ANNs relies on correct weights. However, ANN designers do not generally know which weights will work for a given application. Instead, a training process is used to arrive at appropriate weights. ANN designers typically choose a number of neuron layers or specific connections between layers including circular connection, but the ANN designer does not generally know which weights will work for a given application. Instead, a training process generally proceeds by selecting initial weights, which may be randomly selected. Training data is fed into the ANN and results are compared to an objective function that provides an indication of error. The error indication is a measure of how wrong the ANN's result was compared to an expected result. This error is then used to correct the weights. Over many iterations, the weights will collectively converge to encode the operational data into the ANN. This process may be called an optimization of the objective function (e.g., a cost or loss function), whereby the cost or loss is minimized.

A gradient descent technique is often used to perform the objective function optimization. A gradient (e.g., partial derivative) is computed with respect to layer parameters (e.g., aspects of the weight) to provide a direction, and possibly a degree, of correction, but does not result in a single correction to set the weight to a "correct" value. That is, via several iterations, the weight will move towards the "correct," or operationally useful, value. In some implementations, the amount, or step size, of movement is fixed (e.g., the same from iteration to iteration). Small step sizes tend to take a long time to converge, whereas large step sizes may oscillate around the correct value, or exhibit other undesirable behavior. Variable step sizes may be attempted to provide faster convergence without the downsides of large step sizes.

Backpropagation is a technique whereby training data is fed forward through the ANN—here "forward" means that the data starts at the input neurons and follows the directed graph of neuron connections until the output neurons are reached—and the objective function is applied backwards through the ANN to correct the synapse weights. At each step in the backpropagation process, the result of the previous step is used to correct a weight. Thus, the result of the output neuron correction is applied to a neuron that connects to the output neuron, and so forth until the input neurons are reached. Backpropagation has become a popular technique to train a variety of ANNs.

In one example, training data may comprise sampled values of one or more of the curves shown in FIG. 6. The sampling rate may be varied in different examples such as every 0.1 seconds or 0.001 seconds. The sampled values may be provided to a deep neural network or other suitable network for generation of a model to classify the sampled signals. In one embodiment, the sampling rate may be set to obtain a number of values over a desired time that corresponds to the width of the input to the network. The resulting model may be used to classify telemetry from new hammer strikes.

Figure 7:
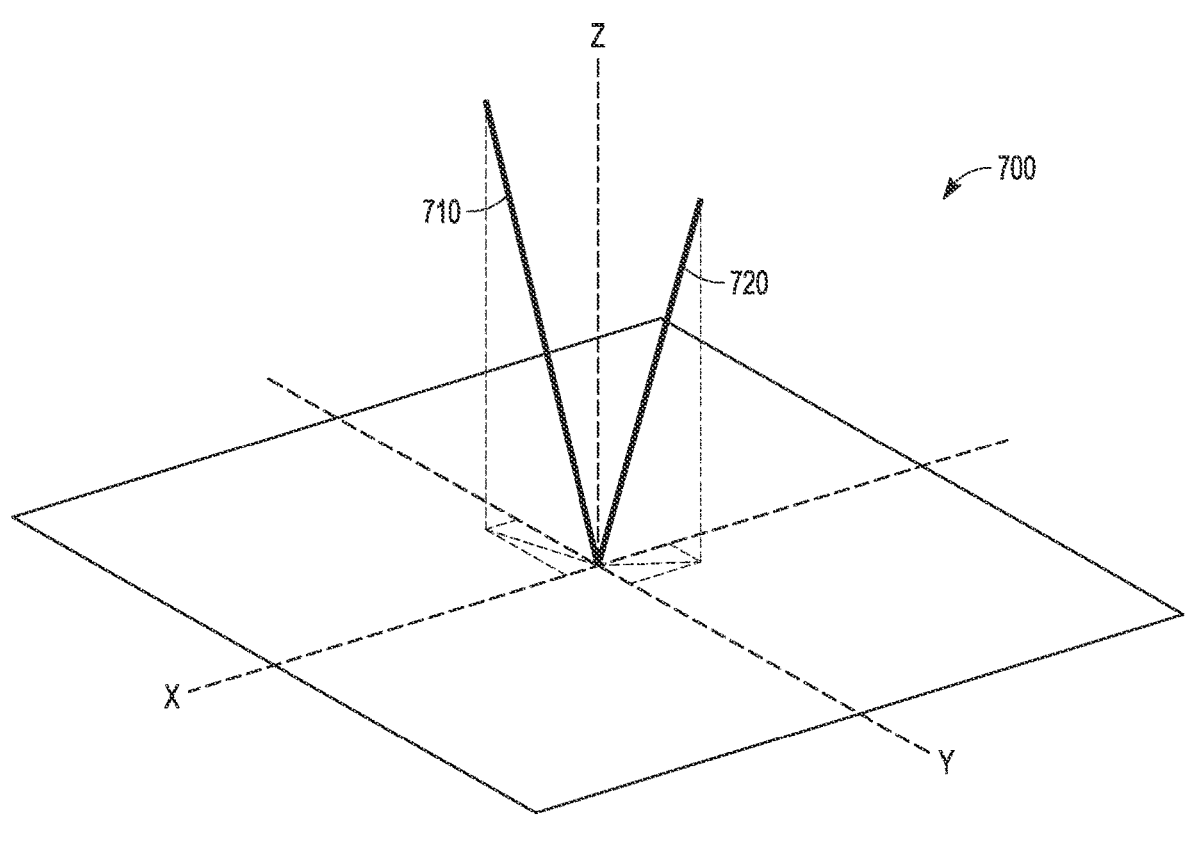
FIG. 7 is a graph illustrating three-dimensional metrics corresponding to hammer strikes according to an example embodiment.

FIG. 7 is a graph 700 illustrating three-dimensional metrics including relative, absolute, and differential magnitudes and direction of inbound 710 and rebound 720 hammer 100 strikes, as well as forward and return path device 315 vectors. x,y,z angles and angle differentials can be used for "trueness factor" derivation of standardizing patient responses, compensation for indirect hits or glancing blows. This metric can also be used for a "Q" or quality factor for each hit, which can be tied to hammer visual indication/LED color for strength, quality, or a combination thereof using different colors and/or sequences. Such a metric can the be used to either accept or discard data, and to normalize data for varying degrees of acceptable hammer strikes.

Figure 8:
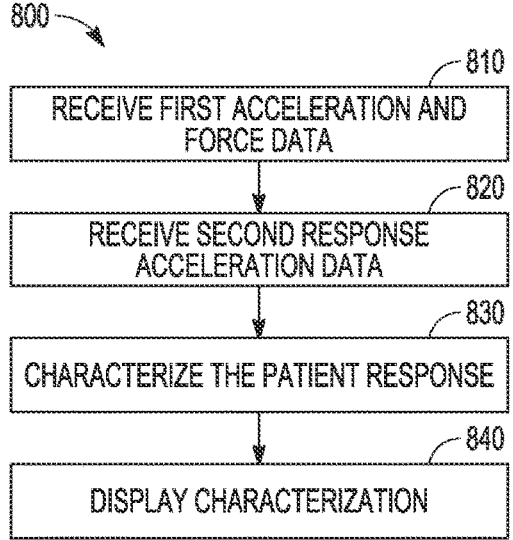
FIG. 8 is a flowchart illustrating a method or processing data corresponding to hammer strikes according to an example embodiment.

FIG. 8 is a flowchart illustrating a method 800 of processing data corresponding to hammer strikes according to an example embodiment. Method 800 includes multiple operations implemented in computer code stored on a memory device. The code may be executed by a processor to perform operations. At operation 810, first acceleration data and force data are received from a first accelerometer and force sensor of the reflex hammer that is used to strike a patient tendon. Second acceleration data is received from a second accelerometer coupled to a limb of the patient in response to the strike of the patient tendon at operation 820. The collected data is processed at operation 830 to characterize the patient response to the strike. Operation 840 may be performed to display a representation of the characterized patient response, such as by use of an LED or other type of display.

Operation 830 may include determining a time of strike of the tendon based on the acceleration data collected from the first accelerometer, determining a time of patient response based on the acceleration data collected from the second accelerometer, determining a delay of response from the first and second acceleration data.

The second acceleration data may be received from a monitor device having an accelerometer via a wireless transmission and may be synchronized with the first acceleration data.

In further embodiments, method 800 may determine a magnitude and angle of approach to strike and magnitude and angle of strike rebound with respect to the patient tendon as a function of the first acceleration data and force data. Method 800 may also determine whether the strike was an indirect or glancing blow.

Figure 9:
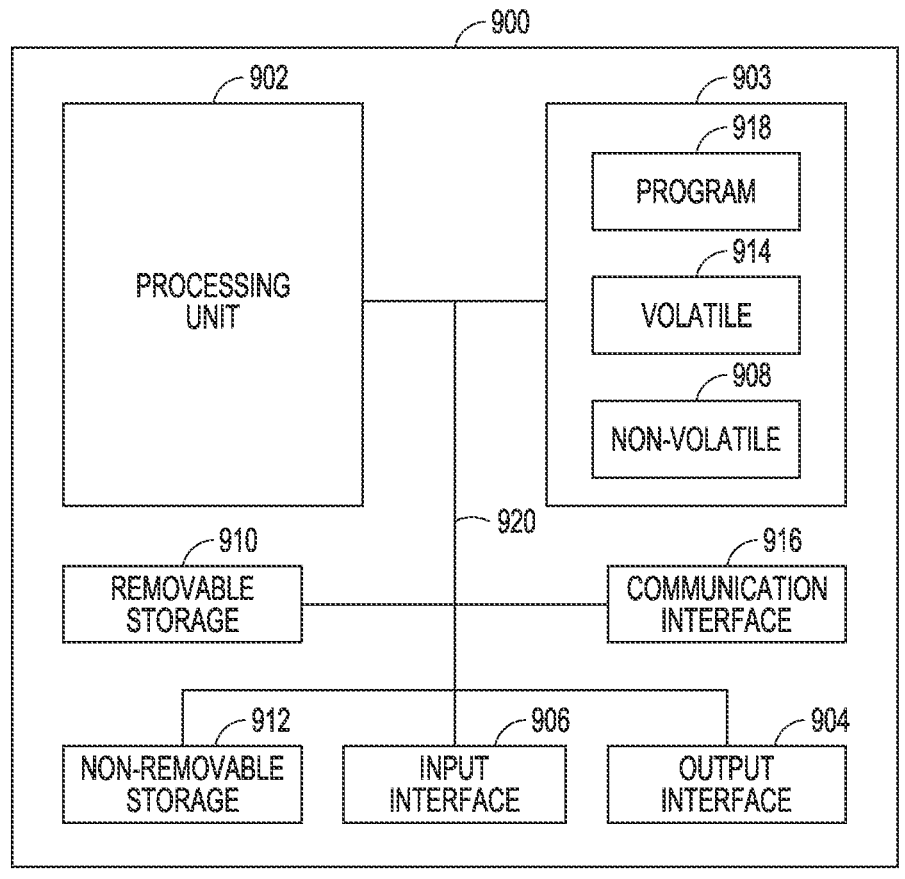
FIG. 9 is a block schematic diagram of a computer system to implement one or more example embodiments.

FIG. 9 is a block schematic diagram of a computer system 900 to receive data from sensors, process the data, and perform methods and algorithms according to example embodiments. All components need not be used in various embodiments.

One example computing device in the form of a computer 900 may include a processing unit 902, memory 903, removable storage 910, and non-removable storage 912. Although the example computing device is illustrated and described as computer 900, the computing device may be in different forms in different embodiments. For example, the computing device may instead be a smartphone, a tablet, smartwatch, smart storage device (SSD), or other computing device including the same or similar elements as illustrated and described with regard to FIG. 9. Devices, such as smartphones, tablets, and smartwatches, are generally collectively referred to as mobile devices or user equipment.

Although the various data storage elements are illustrated as part of the computer 900, the storage may also or alternatively include cloud-based storage accessible via a network, such as the Internet or server-based storage. Note also that an SSD may include a processor on which the parser may be run, allowing transfer of parsed, filtered data through I/O channels between the SSD and main memory.

Memory 903 may include volatile memory 914 and non-volatile memory 908. Computer 900 may include—or have access to a computing environment that includes—a variety of computer-readable media, such as volatile memory 914 and non-volatile memory 908, removable storage 910 and non-removable storage 912. Computer storage includes random access memory (RAM), read only memory (ROM), erasable programmable read-only memory (EPROM) or electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions.

Computer 900 may include or have access to a computing environment that includes input interface 906, output interface 904, and a communication interface 916. Output interface 904 may include a display device, such as a touchscreen, that also may serve as an input device. The input interface 906 may include one or more of a touchscreen, touchpad, mouse, keyboard, camera, one or more device-specific buttons, one or more sensors integrated within or coupled via wired or wireless data connections to the computer 900, and other input devices. The computer may operate in a networked environment using a communication connection to connect to one or more remote computers, such as database servers. The remote computer may include a personal computer (PC), server, router, network PC, a peer device or other common data flow network switch, or the like. The communication connection may include a Local Area Network (LAN), a Wide Area Network (WAN), cellular, Wi-Fi, Bluetooth, or other networks. According to one embodiment, the various components of computer 900 are connected with a system bus 920.

Computer-readable instructions stored on a computer-readable medium are executable by the processing unit 902 of the computer 900, such as a program 918. The program 918 in some embodiments comprises software to implement one or more methods described herein. A hard drive, CD-ROM, and RAM are some examples of articles including a non-transitory computer-readable medium such as a storage device. The terms computer-readable medium and storage device do not include carrier waves to the extent carrier waves are deemed too transitory. Storage can also include networked storage, such as a storage area network (SAN). Computer program 918 along with the workspace manager 922 may be used to cause processing unit 902 to perform one or more methods or algorithms described herein.

EXAMPLES

1. A system includes a first device that has a handle, a head coupled to the handle, a bumper supported by a first end of the head and adapted to be used to strike a patient tendon, a force sensor coupled to the bumper and adapted to generate force data in response to force encountered by the bumper and to generate force data, a first accelerometer coupled to generate head acceleration data in response to movement of the head, and first circuitry to capture the force data and acceleration data.

2. The system of example 1 and further including a second device having a housing adapted to be coupled to the patient limb, a second accelerometer supported by the housing to generate limb acceleration data, and second circuitry to capture the acceleration data.

3. The system of example 2 wherein the first and second circuitry each include a wireless transceiver to wirelessly connect the first and second devices.

4. The system of example 3 wherein the first and second circuitry are synchronized in time to provide a time of impact on the patient tendon and a time of response for calculation of a delay of response.

5. The system of any of examples 1-4 wherein the first device includes a first display coupled to the first circuitry.

6. The system of example 5 wherein the first circuitry is configured to provide a status indication via the first display.

7. The system of any of examples 1-6 wherein the first circuitry is configured to generate a peak head velocity value from the first acceleration data.

8. The system of any of examples 1-7 wherein the first circuitry is configured to generate a time of impact value.

9. The system of any of examples 1-8 wherein the first accelerometer includes a six degree of freedom accelerometer and wherein the head acceleration data and force data is representative of magnitude and angle of approach to strike and magnitude and angle of strike rebound with respect to the patient tendon.

10. The system of example 9 wherein the circuitry is configured to determine indirect or glancing strikes as a function of the head acceleration data.

11. A computer implemented method includes receiving first acceleration data and force data from a first accelerometer and force sensor of a reflex hammer used to strike a patient tendon, receiving second acceleration data from a second accelerometer coupled to a limb of the patient in response to the strike of the patient tendon, and processing the collected data to characterize the patient response to the strike.

12. The method of example 11 wherein processing the data includes determining a time of strike of the tendon based on the acceleration data collected from the first accelerometer, determining a time of patient response based on the acceleration data collected from the second accelerometer, and determining a delay of response from the first and second acceleration data.

13. The method of any of examples 11-12 wherein the second acceleration data is received via a wireless transmission.

14. The method of any of examples 11-13 wherein the first acceleration data and force data is synchronized with the second acceleration data.

15. The method of any of examples 11-14 and further comprising displaying a representation of the characterized patient response.

16. The method of any of examples 11-15 and further comprising determining a magnitude and angle of approach to strike and magnitude and angle of strike rebound with respect to the patient tendon as a function of the first acceleration data and force data.

17. The method of example 16 and further comprising determining whether the strike was an indirect or glancing blow.

18. A machine-readable storage device has instructions for execution by a processor of a machine to cause the processor to perform operations to perform a method. The operations include determining a time of strike of the tendon based on the acceleration data collected from the first accelerometer, determining a time of patient response based on the acceleration data collected from the second accelerometer, and determining a delay of response from the first and second acceleration data.

19. The device of example 18 wherein the second acceleration data is received via a wireless transmission and wherein the first acceleration data and force data is synchronized with the second acceleration data.

20. The device of any of examples 18-19 wherein the operations further include determining a magnitude and angle of approach to strike and magnitude and angle of strike rebound with respect to the patient tendon as a function of the first acceleration data and force data, and determining whether the strike was an indirect or glancing blow.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A system includes:

a deep tendon reflex hammer comprising:

a handle;

a head coupled to the handle;

a bumper supported by a first end of the head and adapted to be used to strike a patient tendon;

a pressure sensor embedded in material of the bumper and adapted to generate pressure data in response to and representative of pressure encountered by the bumper;

a first accelerometer coupled to generate head acceleration data in response to movement of the head, wherein the first accelerometer comprises a six degree of freedom accelerometer and wherein the head acceleration data and pressure data is representative of magnitude and angle of approach to strike and magnitude and angle of strike rebound with respect to the patient tendon representative of a validity of the strike; and first circuitry to capture the pressure data and head acceleration data and coordinate the data to a synchronization pulse from which strike magnitude and angle and rebound magnitude and angle is calculatable to determine a valid tendon strike; and a second device comprising:

a housing adapted to be coupled to a patient limb;

a second accelerometer supported by the housing to generate limb acceleration data; and second circuitry to capture the limb acceleration data and coordinate the data to the synchronization pulse, wherein the generated and captured data enables deep tendon reflex assessment, and wherein an acceptable strike is determined based the pressure data and the head acceleration data.

2. The system of claim 1 wherein the first and second circuitry each include a wireless transceiver to wirelessly connect the first and second circuitry.

3. The system of claim 2 wherein the first and second circuitry are synchronized in time via the synchronization pulse to provide a time of impact on the patient tendon and a time of response for calculation of a delay of response.

4. The system of claim 1 wherein the first device includes a first display coupled to the first circuitry.

5. The system of claim 4 wherein the first circuitry is configured to provide a status indication via the first display representative of the validity of the strike.

6. The system of claim 1 wherein the first circuitry is configured to generate a peak head velocity value from the first acceleration data.

7. The system of claim 1 wherein the first circuitry includes a synchronized clock.

8. The system of claim 1 wherein the first circuitry is configured to determine indirect or glancing strikes as a function of the head acceleration data.

9. The system of claim 1 wherein the bumper is formed of compliant material and the pressure sensor is embedded within the compliant material of the bumper to detect an amount of pressure the bumper encounters in response during contacting a tendon of a patient.

10. The system of claim 1 wherein the bumper is formed of compliant material to consistently transfer pressure from the bumper contacting a tendon of a patient to the pressure sensor.

11. The system of claim 1 wherein the pressure sensor comprises multiple pressure sensors with different pressure ranges.

12. The system of claim 1 wherein the pressure sensor comprises multiple layered pressure sensors with different pressure ranges.

13. A deep tendon reflex hammer comprising:

a handle;

a head coupled to the handle;

a bumper supported by a first end of the head and adapted to be used to strike a patient tendon;

a pressure sensor embedded within material of the bumper and adapted to generate pressure data in response to and representative of pressure encountered by the bumper;

a first accelerometer supported within the head to generate head acceleration data in response to movement of the head, wherein the first accelerometer comprises a six degree of freedom accelerometer and wherein the head acceleration data and pressure data is representative of magnitude and angle of approach to strike and magnitude and angle of strike rebound with respect to the patient tendon representative of a validity of the strike; and first circuitry to capture the pressure data and acceleration data with absolute time information based on a synchronization pulse to determine validity of the strike based on strike magnitude and angle and rebound magnitude and angle wherein an acceptable strike is determined based on the pressure data and the head acceleration data.

14. The reflex hammer of claim 13 and further including a second device comprising:

a housing adapted to be coupled to a patient limb;

a second accelerometer supported by the housing to generate limb acceleration data; and second circuitry to capture the acceleration data with absolute time information based on the synchronization pulse.

15. The reflex hammer of claim 14 wherein the first and second circuitry each include a wireless transceiver to wirelessly connect the first and second devices.

16. The reflex hammer of claim 15 wherein the first and second circuitry are synchronized in time to provide a time of impact on the patient tendon and a time of response for calculation of a delay of response.

17. The reflex hammer of claim 13 and further comprising a first display coupled to the first circuitry.

18. The reflex hammer of claim 17 wherein the first circuitry is configured to provide a status indication via the first display.

* * * * *